United States Patent
Minetoma

(10) Patent No.: US 8,303,494 B2
(45) Date of Patent: Nov. 6, 2012

(54) ELECTRONIC ENDOSCOPE SYSTEM, PROCESSING APPARATUS FOR ELECTRONIC ENDOSCOPE, AND IMAGE PROCESSING METHOD

(75) Inventor: Yasuhiro Minetoma, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 259 days.

(21) Appl. No.: 12/940,625

(22) Filed: Nov. 5, 2010

(65) Prior Publication Data
US 2011/0112362 A1 May 12, 2011

(30) Foreign Application Priority Data

Nov. 6, 2009 (JP) ................................. 2009-255160

(51) Int. Cl.
*A61B 1/04* (2006.01)
*A61B 1/06* (2006.01)
(52) U.S. Cl. .......................... 600/178; 600/160; 600/476
(58) Field of Classification Search .................. 600/178, 600/160, 109, 181, 476, 180
See application file for complete search history.

(56) References Cited

U.S. PATENT DOCUMENTS

| | | | |
|---|---|---|---|
| 7,037,259 B2 * | 5/2006 | Hakamata et al. | 600/178 |
| 7,667,180 B2 * | 2/2010 | Maeda | 250/208.1 |
| 8,107,158 B2 * | 1/2012 | Yamazaki et al. | 359/292 |
| 2003/0176768 A1 * | 9/2003 | Gono et al. | 600/109 |
| 2003/0229270 A1 * | 12/2003 | Suzuki et al. | 600/178 |
| 2005/0234302 A1 * | 10/2005 | MacKinnon et al. | 600/181 |
| 2005/0267374 A1 * | 12/2005 | Yokomise et al. | 600/476 |
| 2007/0153542 A1 * | 7/2007 | Gono et al. | 362/574 |
| 2008/0281154 A1 * | 11/2008 | Gono et al. | 600/109 |
| 2009/0023991 A1 * | 1/2009 | Gono et al. | 600/109 |
| 2009/0124854 A1 * | 5/2009 | Yamaguchi et al. | 600/109 |
| 2011/0071352 A1 * | 3/2011 | Ozawa et al. | 600/109 |
| 2011/0071353 A1 * | 3/2011 | Ozawa et al. | 600/109 |

FOREIGN PATENT DOCUMENTS

| | | |
|---|---|---|
| EP | 1302152 A1 | 4/2003 |
| EP | 1488731 A1 | 12/2004 |
| EP | 1787577 A1 | 5/2007 |
| EP | 1880657 A1 | 1/2008 |
| JP | 3559755 B2 | 9/2004 |

* cited by examiner

*Primary Examiner* — John P Leubecker
(74) *Attorney, Agent, or Firm* — Birch, Stewart, Kolasch & Birch, LLP

(57) ABSTRACT

An image of a tissue site including a blood vessel is captured while broadband light and narrow band light are emitted to a body cavity. Thereby, broadband image data corresponding to the broadband light and narrow band image data corresponding to the narrow band light are obtained. Picture elements in the same positions are identified between the broadband image and the narrow band image to obtain a brightness ratio LM therebetween. Based on depth correlation information between the brightness ratio and blood vessel depth, a blood vessel depth D corresponding to the brightness ratio is obtained to determine whether each picture element includes a blood vessel and whether the blood vessel depth D is at the surface. Based on the determination, a surface blood vessel region is extracted. A broadband image having the surface blood vessel region with the reduced contrast is generated.

9 Claims, 7 Drawing Sheets

ELECTRONIC ENDOSCOPE SYSTEM, PROCESSING APPARATUS FOR ELECTRONIC ENDOSCOPE, AND IMAGE PROCESSING METHOD

FIELD OF THE INVENTION

The present invention relates to an electronic endoscope system for use in observation of a body cavity, a processing apparatus for an electronic endoscope, and a signal separation method.

BACKGROUND OF THE INVENTION

Recently, diagnoses and medical treatments using electronic endoscopes are commonly performed in the medical field. An electronic endoscope has a long insert section to be inserted into a patient's body cavity. The electronic endoscope incorporates an imaging device such as a CCD at its distal end. The electronic endoscope is connected to a light source apparatus. The light source apparatus delivers light to the electronic endoscope via a light guide such as an optical fiber. The electronic endoscope emits the light from its distal end to illuminate the body cavity. The imaging device at the distal end of the insert section captures an image of a tissue site in the body cavity while the body cavity is illuminated. The image is subjected to various processes in a processing apparatus connected to the electronic endoscope, and then displayed on a monitor. With the use of the electronic endoscope, a doctor can observe an image of the tissue site in the patient's body cavity real-time, which ensures accurate diagnosis.

The light source apparatus is a white light source, for example, a xenon lamp that emits white broadband light in a wavelength range from blue to red. An image (hereafter referred to as broadband image) captured with the illumination of the white broadband light shows the overall condition of the tissue site, for example, mucosa located on a surface of the tissue site, blood vessels inside the tissue, the shape and condition of the surface of the mucosa such as protrusion or depression, and the presence or absence of polyp.

In addition to the observation of the broadband image (normal visible image), observation with "special light", that is, the observation using a narrow band light source that emits narrow band light in a specific wavelength range is performed as disclosed in Japanese Patent No. 3559755 corresponding to U.S. Patent No. 2003/0176768, for example. Light penetrates deeper into the tissue site as its wavelength increases, namely, blue light, green light, and red light increase in penetration depth in this order. Using the difference in the penetration depth, the endoscope system of Japanese Patent No. 3559755 generates a narrow band image in which blood vessels at a specific depth (for example, at the surface or at the depths) are enhanced. For example, with the emission of blue narrow band light having a small penetration depth, a narrow band image is generated with an enhanced surface blood vessel region. With the emission of green narrow band light having the penetration depth larger than that of the blue narrow band light, a narrow band image is generated with enhanced blood vessels located at the depth deeper than the surface. Thus, the blood vessels at a specific depth are more clearly observed in the narrow band image than in the broadband image.

Although the narrow band image of Japanese Patent No. 3559755 enhances the blood vessels, visibility of a region other than the blood vessels, such as the condition of mucosa, the shape of the mucosal surface, or the presence or absence of polyp, becomes significantly low when compared to the broadband image, because the narrow band image is a monochrome image using narrow band light of a single color. To observe the blood vessel region and the remaining region at a time, the narrow band image and the broadband image are displayed on the monitor side by side. The doctor needs to move his or her eyes between the narrow band image and the broadband image. Accordingly, the two images cannot be observed at a glance and cannot be easily contrasted with each other.

In the case where the region of interest is not the blood vessels, it becomes easy to observe the region of interest when the blood vessels are inconspicuous. The blood vessels are inconspicuous in the broadband image compared to those in the narrow band image. However, within the broadband image, the blood vessels, especially, the surface blood vessels are conspicuous compared to the remaining region, interfering with the observation of the remaining region. To solve this problem, visibility of the surface blood vessels needs to be reduced. For example, a pattern analysis may be performed to the broadband image to identify the position of the blood vessel region to reduce the contrast and visibility thereof.

However, the broadband image includes a considerable amount of information other than that of the blood vessels. The above method using the pattern analysis has poor accuracy because there is a high possibility that a region other than the blood vessels may be mistaken as the blood vessels.

Even if the blood vessel region is identified using the pattern analysis of the broadband image, the depth of the blood vessels cannot be determined, for example, the surface blood vessels cannot be distinguished from the deep blood vessels. Accordingly, reducing the contrast of one blood vessel region (for example, the surface blood vessel region) also reduces all the other blood vessel regions in the broadband image. The deep blood vessels are naturally inconspicuous compared to the surface blood vessels, so the need of the contrast reduction of the deep blood vessels is rare. If the contrast of the deep blood vessels is reduced, information essential to the deep blood vessels may be lost.

SUMMARY OF THE INVENTION

An object of the present invention is to provide an electronic endoscope system for performing image processing, with high accuracy and without causing loss of at-a-glance property and contrast, to a blood vessel region located at a specific depth or to a region other than the blood vessel region in an image captured with an electronic endoscope, a processing apparatus for the electronic endoscope, and an image processing method.

In order to achieve the above and other objects, the electronic endoscope system of the present invention includes an emission section, an imaging section, a data obtaining section, a brightness ratio calculator, a depth correlation information storage, a depth determining section, a blood vessel region extractor, and an image processing section. The emission section emits white broadband light and narrow band light simultaneously or sequentially to illuminate a tissue site in a body cavity. The tissue site includes a blood vessel. The broadband light has a wavelength range from blue to red. The narrow band light is in a specific wavelength range. The imaging section captures an image of the tissue site during the illumination and outputs image signals in time order. A blue pixel, a green pixel, and a red pixel are arranged in the imaging section. The blue pixel senses blue light to generate a blue color signal. The green pixel senses green light to generate a green color signal. The red pixel senses red light to generate a red color signal. Based on the image signals, the data obtaining section obtains broadband image data and narrow band image data, or mixed image data. The broadband image data corresponds to the image capture under the broadband light. The narrow band image data corresponds to the image capture under the narrow band light. The mixed image data is a combination of the broadband image data and the narrow band image data. The brightness ratio calculator calculates a brightness ratio between the broadband image data and the narrow band image data or a brightness ratio between the blue color signal and the green color signal in the mixed image data on a picture element basis. The depth correlation information storage stores depth correlation information between the brightness ratio and a depth of the blood vessel. The depth determining section refers to the depth correlation information to determine whether the picture element includes the blood vessel and the depth of the blood vessel on the picture element basis with the use of the calculated brightness ratio. The blood vessel region extractor extracts a specific blood vessel region based on the determined depth of the blood vessel. The image processing section performs image processing to the specific blood vessel region or a region other than the specific blood vessel region within a broadband image based on the broadband image data.

It is preferable that the electronic endoscope system further includes an electronic endoscope, a processing apparatus connected to the electronic endoscope, and a light source apparatus. It is preferable that the electronic endoscope is provided with the emission section and the imaging section. It is preferable that the processing apparatus is provided with the data obtaining section, the brightness ratio calculator, the depth correlation information storage, the depth determining section, the blood vessel region extractor, and the image processing section. It is preferable that the light source apparatus is provided with a light source for generating the broadband light and the narrow band light, and the broadband light and the narrow band light are guided to the emission section through a light guide in the electronic endoscope and emitted from the emission section to the tissue site.

It is preferable that the specific blood vessel region is a surface blood vessel located at the small depth.

It is preferable that the image processing is reduction of visibility. It is preferable that to the reduction of the visibility is to reduce contrast.

It is preferable that the broadband light is in a wavelength range from approximately 470 nm to 700 nm, and the narrow band light is in a wavelength range of 440±10 nm or 400±10 nm.

It is preferable that the electronic endoscope system further includes a display section for displaying the broadband image processed in the image processing section.

A processing apparatus connected to an electronic endoscope includes a data obtaining section, a brightness ratio calculator, a depth correlation information storage, a depth determining section, a blood vessel region extractor, and an image processing section. Based on the image signals, the data obtaining section obtains broadband image data and narrow band image data, or mixed image data. The broadband image data corresponds to the image capture under the broadband light. The narrow band image data corresponds to the image capture under the narrow band light. The mixed image data is a combination of the broadband image data and the narrow band image data. The brightness ratio calculator calculates a brightness ratio between the broadband image data and the narrow band image data or a brightness ratio between the blue color signal and the green color signal in the mixed image data on a picture element basis. The depth correlation information storage stores depth correlation information between the brightness ratio and a depth of a blood vessel. The depth determining section refers to the depth correlation information to determine whether the picture element includes the blood vessel and the depth of the determined blood vessel on the picture element basis with the use of the calculated brightness ratio. The blood vessel region extractor extracts a specific blood vessel region based on the determined depth of the blood vessel. The image processing section performs image processing to the specific blood vessel region or a region other than the specific blood vessel region within the broadband image based on the broadband image data.

The image processing method of an endoscopic image includes a signal obtaining step, a data obtaining step, a calculating step, a determining step, an extracting step, and a processing step. In the signal obtaining step, an image of a tissue site in a body cavity is captured while white broadband light in a wavelength range from blue to red and narrow band light in a specific wavelength range are emitted thereto simultaneously or sequentially to obtain image signals in time order. The tissue site includes a blood vessel. The image signals include a blue color signal, a green color signal, and a red color signal. In the data obtaining step, based on the image signals, mixed image data or broadband image data and narrow band image data are obtained. The broadband image data corresponds to the image capture under the broadband light. The narrow band image data corresponds to the image capture under the narrow band light. The mixed image data is a combination of the broadband image data and the narrow band image data. In the calculating step, a brightness ratio between the broadband image data and the narrow band image data or a brightness ratio between the blue color signal and the green color signal in the mixed image data is calculated on a picture element basis. In the determining step, depth correlation information between the brightness ratio and a depth of the blood vessel is referred to, and based on the calculated brightness ratio, whether the picture element includes the blood vessel and the depth of the blood vessel are determined on the picture element basis. In the extracting step, a specific blood vessel region is extracted based on the determined depth of the blood vessel. In the processing step, image processing is performed to the specific blood vessel region or a region other than the specific blood vessel region within the broadband image based on the broadband image data.

According to the present invention, the depth correlation information of the blood vessel depth relative to the brightness ratio between the broadband image data and the narrow band image data or the brightness ratio between the blue color signal and the green color signal of the mixed image data is used. Accordingly, the specific blood vessel region located at a desired depth is extracted accurately. Image processing, for example, contrast reduction processing is performed to the specific blood vessel region, for example, a surface blood vessel or a region other than the specific blood vessel region on the broadband image (visible light image). Thus, an endoscopic image in which the surface blood vessel or the region other than the surface blood vessel is easily observable is obtained.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
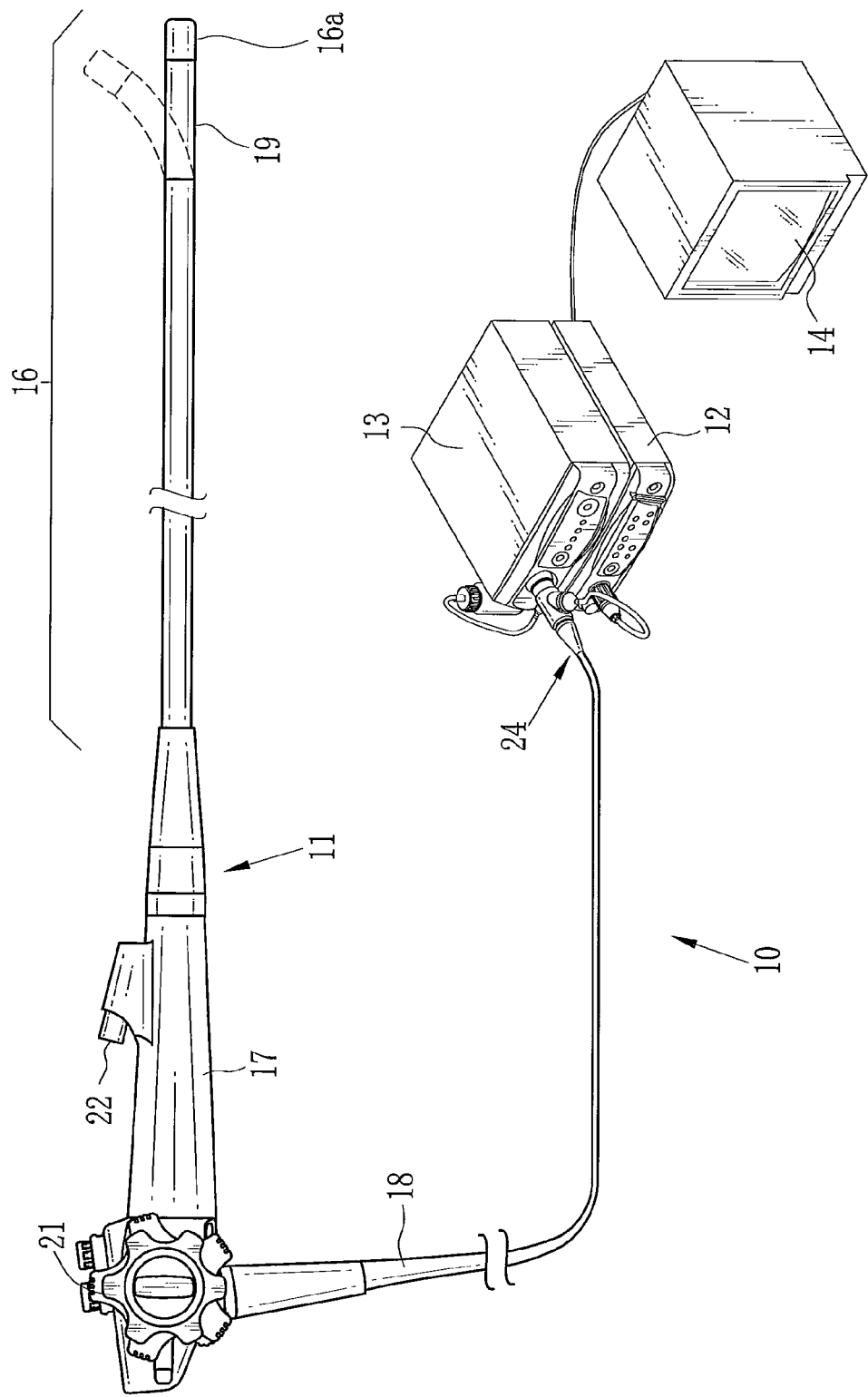
FIG. 1 is an external view of an electronic endoscope system according to the present invention.

As shown in FIG. 1, an electronic endoscope system 10 of the present invention is provided with an electronic endoscope 11, a processing apparatus 12, a light source apparatus 13, and a monitor 14. The electronic endoscope 11 captures an image in a patient's body cavity. The processing apparatus 12 generates an image of a tissue site (an object of interest) in the body cavity based on a signal obtained by the image capture. The light source apparatus 13 supplies light for illuminating the body cavity. The monitor 14 displays the generated image. The electronic endoscope 11 is provided with a flexible insert section 16 to be inserted into the body cavity, a handling section 17 provided in the basal portion of the insert section 16, and a universal cord 18. The universal cord 18 connects the handling section 17, the processing apparatus 12, and the light source apparatus 13.

The insert section 16 has a bending portion 19 at its tip. The bending portion 19 has multiple joint pieces. Operating an angle knob 21 provided in the handling section 17 bends the bending portion 19 in horizontal and vertical directions. A distal portion 16a is provided at a distal end of the bending portion 19. The distal portion 16a incorporates an optical system used for the image capture in the body cavity. Bending the bending portion 19 directs the distal portion 16a to a desired direction.

A connector 24 is attached to one end of the universal cord 18 where the processing apparatus 12 and the light source apparatus 13 are to be connected. The connector 24 is a multiple-type connector composed of a communication connector and a light source connector. The electronic endoscope 11 is detachably connected to the processing apparatus 12 and the light source apparatus 13 via the connector 24.

Figure 2:
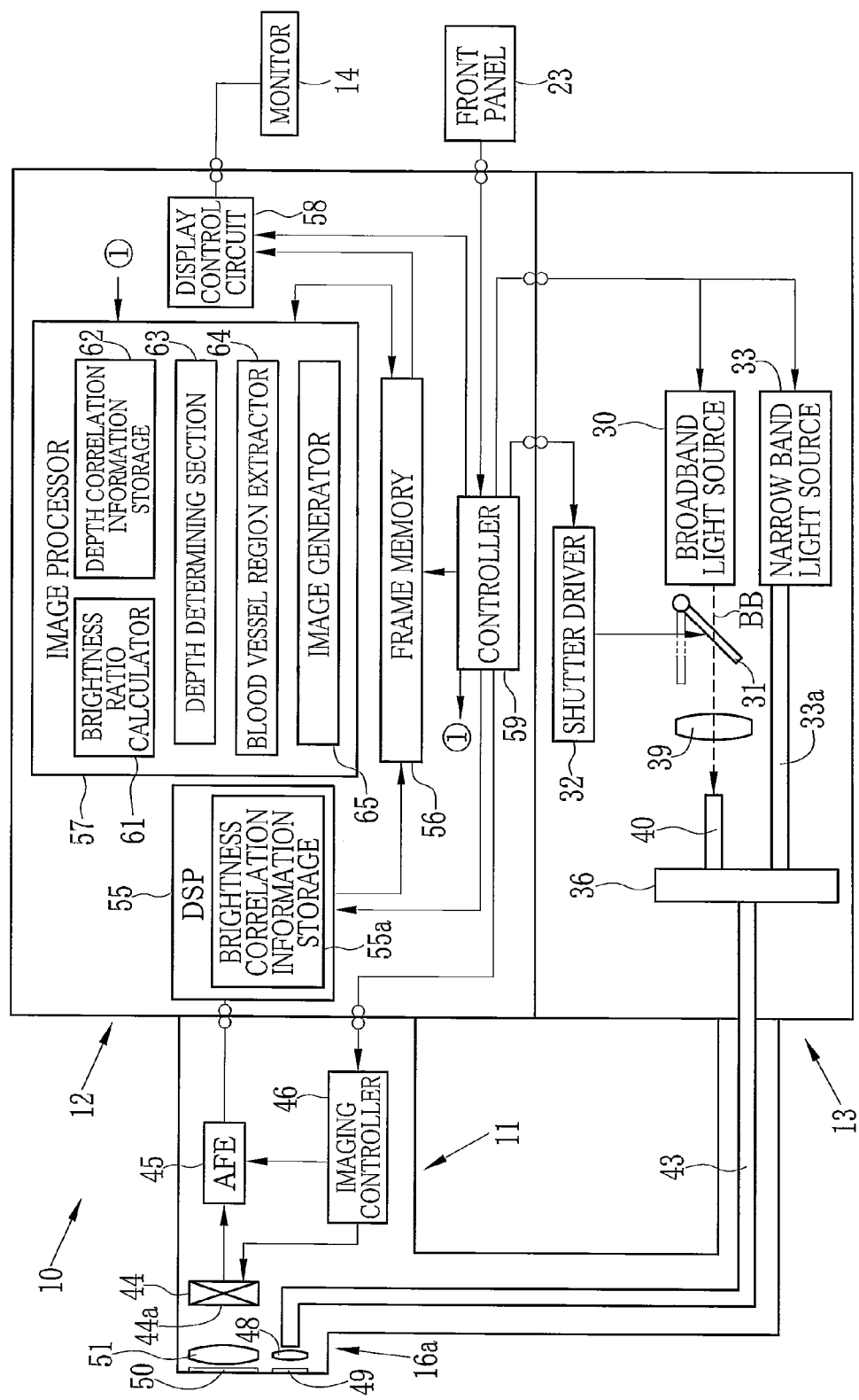
FIG. 2 is a block diagram showing an electric configuration of the electronic endoscope system.

As shown in FIG. 2, the light source apparatus 13 is provided with a broadband light source 30, a shutter 31, a shutter driver 32, a narrow band light source 33, and a coupler 36. The broadband light source 30 is, for example, a xenon lamp that emits broadband light BB in a wavelength range from blue to red (approximately from 470 nm to 700 nm). The broadband light source 30 is kept turned on while the electronic endoscope 11 is in use. The broadband light BB emitted from the broadband light source 30 is gathered or condensed via a condenser lens 39 into a broadband optical fiber 40.

The shutter 31 is provided between the broadband light source 30 and the condenser lens 39. The shutter 31 is movable between an insert position and a retract position. In the insert position, the shutter 31 interferes with or blocks the broadband light BB. In the retract position, the shutter 31 retracts from the insert position to allow the broadband light BB to enter the condenser lens 39. The shutter driver 32 is connected to a controller 59 in the processing apparatus 12, and controls the shutter 31 based on the an instruction from the controller 59.

The narrow band light source 33 is a laser diode, for example. The narrow band light source 33 generates the narrow band light NB in a wavelength range of 440±10 nm, preferably 445 nm. The narrow band light NB is used for determining a blood vessel depth that is the depth or depth information of a blood vessel or a blood vessel region including the blood vessel. The narrow band light source 33 is connected to a narrow band optical fiber 33a, so the light from the narrow band light source 33 enters the narrow band optical fiber 33a. The narrow band light source 33 is also connected to the controller 59 in the processing apparatus 12. Based on an instruction from the controller 59, the narrow band light source 33 is turned on or off. The wavelength range of the narrow band light NB is not limited to 440±10 nm. The narrow band light NB may be in any wavelength range as long as the narrow band light NB is not sensed by the G pixel and R pixel of the CCD 44 (for example, 400±10 nm).

The coupler 36 couples the light guide 43 in the electronic endoscope 11, the broadband optical fiber 40, and the narrow band optical fiber 33a. The coupler 36 allows the broadband light BB to enter the light guide 43 via the broadband optical fiber 40. The coupler 36 allows the narrow band light NB to enter the light guide 43 via the narrow band optical fiber 33a.

In this embodiment, in a normal mode for emitting only the broadband light BB to obtain a broadband image, the shutter 31 is set in a retract position and the narrow band light source 33 is turned off. In a special mode for performing image processing to a blood vessel region in a broadband image, both the broadband light BB and the narrow band light NB are emitted. That is, in the special mode, the shutter 31 is set in the retract position, and the narrow band light source 33 is turned on. To emit the narrow band light only, the shutter 31 is set in the insert position, and the narrow band light source 33 is turned on.

The electronic endoscope 11 is provided with a light guide 43, a CCD 44, an AFE (analog front end) 45, and an imaging controller 46. The light guide 43 is, for example, a large core optical fiber or a bundle fiber, and its input end is inserted into the coupler 36 in the light source apparatus 13 and its exit end is directed to an illumination lens 48 provided at the distal portion 16a. The light guide 43 delivers the light emitted from the light source apparatus 13 to the illumination lens 48. The light enters the illumination lens 48 and then is emitted to the body cavity through an illumination window 49 attached to an end surface of the distal portion 16a. The broadband light BB and the narrow band light NB reflected inside the body cavity enter a focus lens 51 through an image capturing window 50 attached to the end surface of the distal portion 16a. An emission section is composed of the illumination lens 48 and the illumination window 49.

The CCD 44 is a color CCD. On the imaging surface 44a, red, green and blue (R, G, and B) pixels are arranged in matrix. The R pixel is provided with a red filter. The G pixel is provided with a green filter. The B pixel is provided with a blue filter. An imaging surface 44a of the CCD 44 receives the light from the focus lens 51. The received light is photoelectrically converted in each color pixel and accumulated as signal charge. The imaging controller 46 reads the accumulated signal charge as image signals in time order. The read image signals are sent to the AFE 45. The imaging section is composed of the CCD 44, the focus lens 51, and the imaging controller 46.

Figure 3:
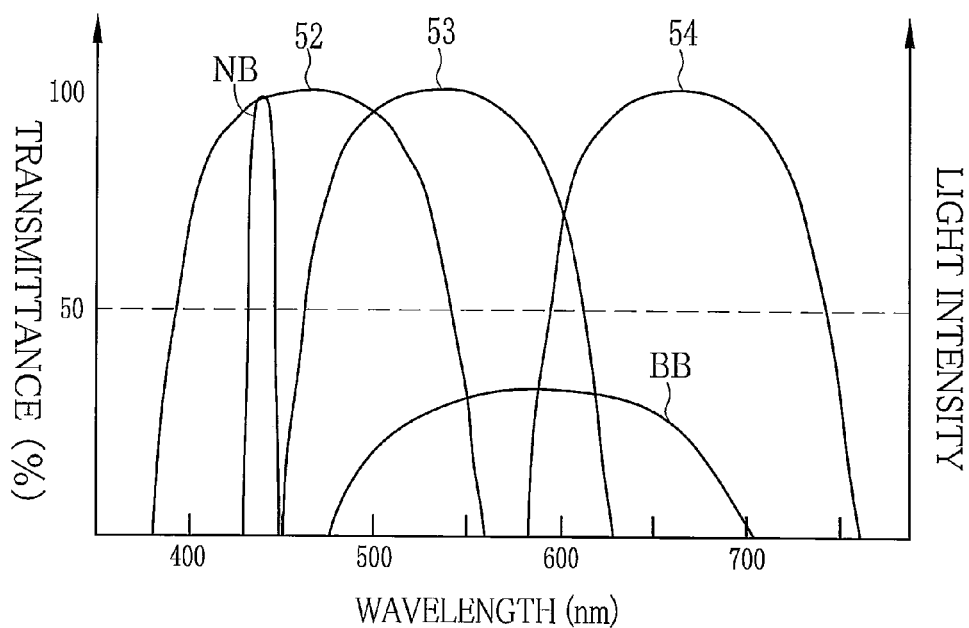
FIG. 3 is a graph showing spectral transmittances of red, green, and blue filters.

The blue filter (B filter), the green filter (G filter), and the red filter (R filter) have spectral transmittances 52, 53, and 54, respectively, as shown in FIG. 3. When only the broadband light BB in a wavelength range from approximately 470 nm to 700 nm enters the CCD 44, the B, G, and R filters transmit or pass the light having wavelengths corresponding to the spectral transmittances 52, 53, and 54, respectively. A signal photoelectrically converted in the R pixel is defined as an R image signal (red color signal). A signal photoelectrically converted in the G pixel is defined as a G image signal (green color signal). A signal photoelectrically converted in the B pixel is defined as a B image signal (blue color signal). In the normal mode, only the broadband light BB enters the CCD 44. Accordingly, a broadband image signal composed of the R, G, and B image signals is obtained.

In the special mode, in addition to the broadband light BB, the narrow band light NB in a wavelength range of 440±10 nm enters the CCD 44. The narrow band light NB only passes through the blue filter (B filter). Accordingly, the B image signal contains the brightness value of the B component of the broadband light BB and a narrow band image signal representing a brightness value of the narrow band light NB. In the special mode, the broadband light BB and the narrow band light NB enters the CCD 44 simultaneously. Thereby, the CCD 44 outputs an image signal composed of the R image signal, the G image signal, and the B image signal in which the brightness value of the B component of the broadband light BB and the brightness value of the narrow band light NB are summed or combined. Hereafter, this image signal is referred to as the mixed image signal.

The AFE 45 is composed of a correlated double sampling circuit (CDS), an automatic gain control circuit (AGC), and an analog/digital converter (A/D) (all not shown). The CDS performs correlated double sampling to the image signal from the CCD 44 to remove noise caused by the CCD 44. Then, the AGC amplifies the image signal. Thereafter, the A/D converts the image signal into a digital image signal (mixed image signal) having a predetermined number of bits and inputs the digital image signal to the processing apparatus 12.

The imaging controller 46 is connected to the controller 59 in the processing apparatus 12. The imaging controller 46 sends a drive signal to the CCD 44 when instructed by the controller 59. Based on the drive signal from the imaging controller 46, the CCD 44 outputs the image signal to the AFE 45 at a predetermined frame rate.

Figure 4A:
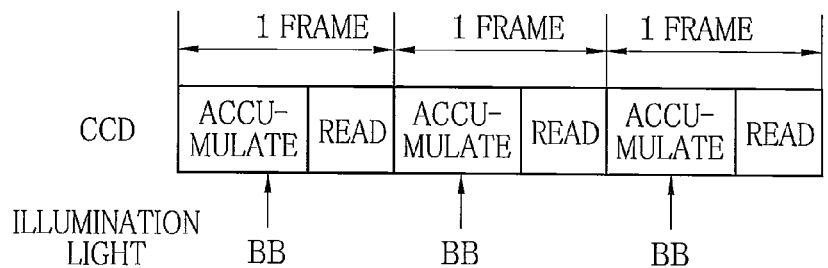
FIG. 4A is an imaging operation of a CCD in a normal mode.

In this embodiment, in the normal mode, an accumulation step and a reading step are performed to acquire one frame of image signal as shown in FIG. 4A. In the accumulation step, the broadband light BB is photoelectrically converted into signal charge and accumulated. In the reading step, the accumulated signal charge is read as a broadband image signal. The accumulation step and the reading step are performed alternately and repeatedly.

Figure 4B:
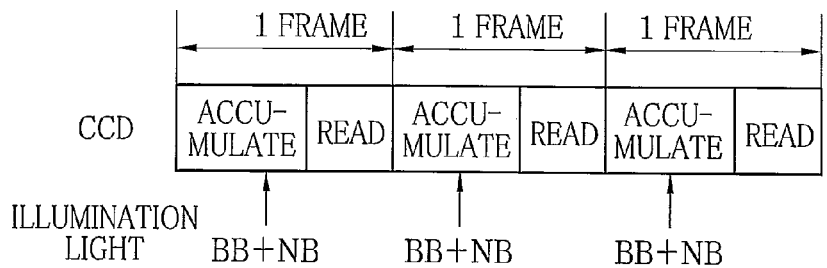
FIG. 4B is an imaging operation of the CCD in a special mode.

In the special mode, a mixed accumulation step and a mixed reading step are performed to acquire one frame of image signal as shown in FIG. 4B. In the mixed accumulation step, the broadband light BB and the narrow band light NB are photoelectrically converted into signal charge and accumulated. In the mixed reading step, the accumulated signal charge is read as a mixed image signal. The mixed accumulation step and the mixed reading step are performed alternately and repeatedly.

As shown in FIG. 2, the processing apparatus 12 is provided with a DSP (Digital Signal Processor) 55, a frame memory 56, an image processor 57, a display controller 58. The controller 59 controls each of the above sections. The DSP 55 performs various signal processes such as color separation, color interpolation, white balance adjustment, and gamma correction to the image signal outputted from the AFE 45 to create image data. A data obtaining section is composed of the DSP 55.

The DSP 55 performs the above signal processes to the broadband image signal to create broadband image data. The broadband image data is stored in the frame memory 56.

The mixed image signal is composed of the R image signal, the G image signal, and the B image signal. The R image signal only has the brightness value Broad_R of the broadband light BB. The G image signal only has the brightness value Broad_G of the broadband light BB. The B image signal is the sum of the brightness value Broad_B of the broadband light BB and the brightness value L1 of the narrow band light NB.

B image signal=brightness value L1+brightness value Broad_B

G image signal=brightness value Broad_G

R image signal=brightness value Broad_R

The DSP 55 is provided with a brightness correlation information storage 55a that stores brightness correlation information among the brightness values Broad_B, Broad_G, and Broad_R. The brightness correlation information is obtained from results of analysis of a plurality of image data used and stored in the past diagnoses, for example. To be more specific, when the white light is emitted to a tissue site in the body cavity and the reflected light is received by the CCD 44, the brightness values of the R, G, and B image signals are correlated to each other. The DSP 55 refers to the brightness correlation information stored in the brightness correlation information storage 55a to obtain the brightness value Broad_B using its correlation with the brightness value Broad_G or Broad_R. Thereby, the DSP 55 obtains the broadband image signal composed of the brightness values Broad_B, Broad_G, and Broad_R from the mixed image signal. This broadband image signal does not include the brightness value L1 of the narrow band light NB. Further, the DSP 55 separates the brightness value Broad_B from the B image signal. Thus, the narrow band image signal only having the brightness value L1 is obtained.

As described above, the DSP 55 separates the mixed image signal into the broadband image signal and the narrow band image signal. The separated broadband image signal and the narrow band image signal are subjected to various signal processes such as color separation, color interpolation, white balance adjustments, and gamma correction. Thus, one frame of broadband image data and one frame of narrow band image data are generated. In the broadband image data, each picture element contains red color data, green color data, and blue color data. In the narrow band image data, on the other hand, each picture element only contains blue color data. The picture elements in the broadband image data correspond to the picture elements in the narrow band image data, respectively. The broadband image data and the narrow band image data are stored in the frame memory 56. Obtaining the broadband image data and the narrow band image data from one frame of mixed image signal has advantages that the perfect registration is achieved between the broadband image and the narrow band image and that it is suitable for capturing moving images, namely, an image is generated using a small number of frames.

The image processor 57 is provided with a brightness ratio calculator 61, a depth correlation information storage 62, a depth determining section 63, a blood vessel region extractor 64, and an image generator 65. The brightness ratio calculator 61 identifies the picture elements in the same positions in the broadband image data and the narrow band image data, respectively, and obtains a brightness ratio LM (S1/S2) between the identified picture elements. The calculation of the brightness ratio LM is performed to every picture elements or on a picture element basis in one frame. The S1 represents the brightness value of the narrow band image data (the signal value of the blue color data). The S2 represents the brightness value Broad_G corresponding to the G component of the broadband light BB having longer wavelengths and larger penetration depth than the narrow band light NB. The narrow band light NB has a small penetration depth, so, a large amount of the narrow band light NB reaches a surface blood vessel region while only a small amount of the narrow band light NB reaches a deep blood vessel region. On the other hand, the G component of the broadband light BB has a large penetration depth, so the amount of light reaching the deep blood vessel region is larger than that of the narrow band light NB. The surface blood vessel region is a blood vessel or blood vessels located at the surface or at a small depth or a region including the blood vessel (s). The deep blood vessel region is a subsurface blood vessel or blood vessels located at the depths or some distance below the surface or a region including the blood vessel (s).

In the tissue site, the blood vessel region absorbs a larger amount of light than the remaining region, so the blood vessel region attenuates both the narrow band light NB and the G component of the broadband light BB incident thereon. Both the narrow band light NB and the G component of the broadband light BB reach the surface blood vessel region. Accordingly, both the brightness value S1 of the narrow band light NB reflected by the surface blood vessel region and the brightness value S2 of the G component of the broadband light BB reflected by the surface blood vessel region become low.

In comparing the brightness values S1 and S2, the brightness value S1 of the reflected narrow band light NB is high because the narrow band light NB does not reach the deep blood vessel region and is mainly reflected by the surface blood vessel region. On the other hand, the brightness value S2 of the reflected G component of the broadband light BB is low because the G component of the broadband light BB reaches the deep blood vessel region. Accordingly, the lower the brightness ratio LM (S1/S2), the smaller the depth (blood vessel depth) of the blood vessel region. The larger the brightness ratio LM (S1/S2), the deeper the blood vessel depth. Thus, in each picture element, the brightness ratio LM between the narrow band light and the broadband light is obtained using the difference in penetration depth. Thus, whether a blood vessel region is included in the picture element or not and a depth of the blood vessel region is determined for each picture element or on a picture element basis.

Figure 5:
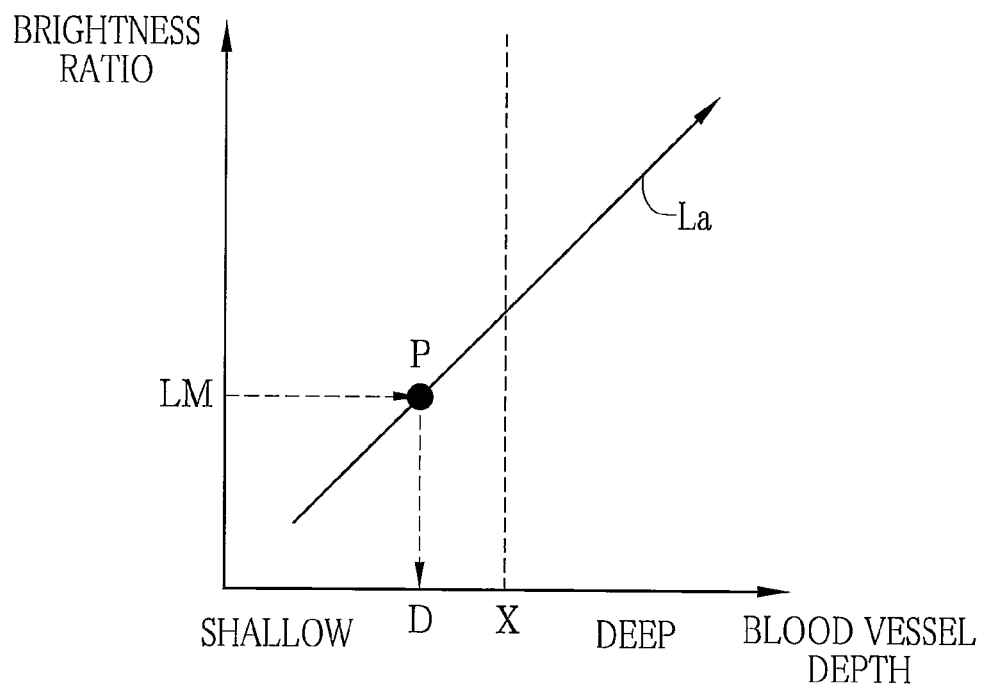
FIG. 5 is a graph showing correlation between a brightness ratio and a depth of a blood vessel.

The depth correlation information storage 62 stores depth correlation information between the brightness ratio LM and the blood vessel depth D. As shown in FIG. 5, the brightness ratio LM and the blood vessel depth D has a positive relationship. The positive relationship is represented by a line segment La having a positive slope in a brightness ratio-blood vessel depth coordinate system. The depth correlation information storage 62 stores the depth correlation information in which the brightness ratio LM and the blood vessel depth D are associated with or correlated with each other on a point P on the line segment La. In the brightness ratio-blood vessel depth coordinate system, an arrow in the vertical axis direction indicates that the brightness ratio increases from the lower end to the upper end, and an arrow in the horizontal axis direction indicates that the blood vessel depth increases from the left end to the right end. "SHALLOW" indicates that the blood vessel depth is shallow. "DEEP" indicates that the blood vessel depth is deep.

Based on the depth correlation information in the depth correlation information storage 62, the depth determining section obtains the blood vessel depth D corresponding to the brightness ratio LM calculated by the brightness ratio calculator 61. The depth determining section 63 compares the blood vessel depth D and a predetermined threshold value X. When the blood vessel depth D is smaller than the threshold value X, the depth determining section 63 determines that the blood vessel depth D is at the surface. When the blood vessel depth D is larger than the threshold value X, the depth determining section 63 determines that the blood vessel depth D is at the depths (subsurface). When the blood vessel depths D in all the picture elements in the broadband image data and the narrow band image data are determined, the blood vessel region extractor 64 reads the broadband image data from the frame memory 56. From the read broadband image data, the blood vessel region extractor 64 extracts the surface blood vessel region and the deep blood vessel region. The surface blood vessel region contains the picture element including the blood vessel determined to be located at the surface or at a small depth. The deep blood vessel region contains the picture element including the blood vessel determined to be located at the subsurface depths or some distance below the surface.

Figure 6:
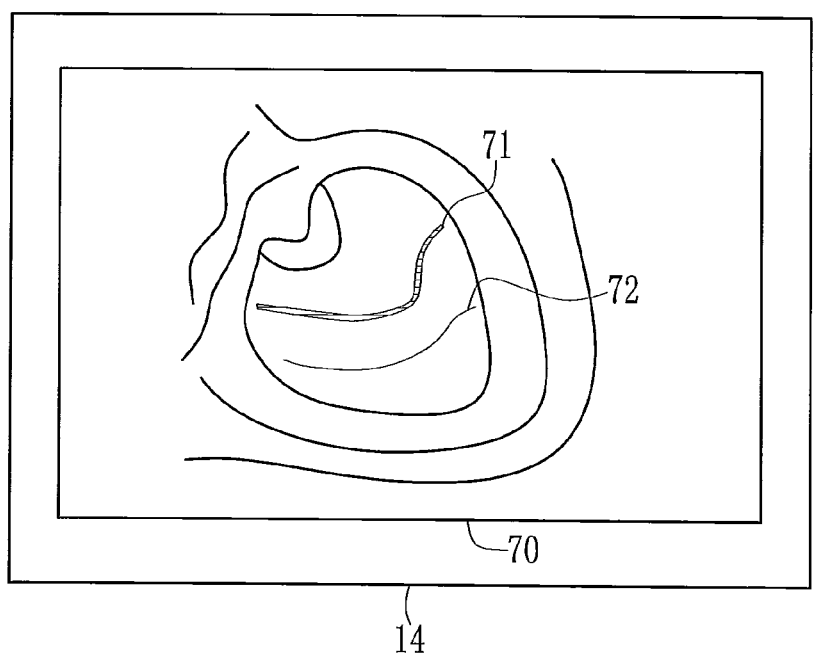
FIG. 6 shows a monitor displaying a broadband image.

As shown in FIG. 6, a broadband image 70 generated based on the broadband image data shows the overall condition of the tissue site including the condition of mucosa on the surface of the tissue site, blood vessels in the tissue site, the shape of the mucosal surface such as protrusions and depressions, and the presence or absence of polyp. From the broadband image 70, the blood vessel region extractor 64 extracts a surface blood vessel region 71 and a deep blood vessel region 72 (subsurface). The surface blood vessel region 71 is displayed clearly and conspicuously compared to the deep blood vessel region 72. In FIG. 6, a thick line depicts the surface blood vessel region 71 with high visibility. A thin line depicts the deep blood vessel region 72 with low visibility.

The image generator 65 performs contrast processing to the broadband image data read from the frame memory 56 to reduce the visibility of the surface blood vessel region 71. The contrast processing is, for example, reduction of contrast in the surface blood vessel region 71 among various types of reduction processing. After the contrast processing, the broadband image data is stored in the frame memory 56. The display controller 58 displays a broadband image 80 on the monitor 14 based on the broadband image data read from the frame memory 56.

Figure 7:
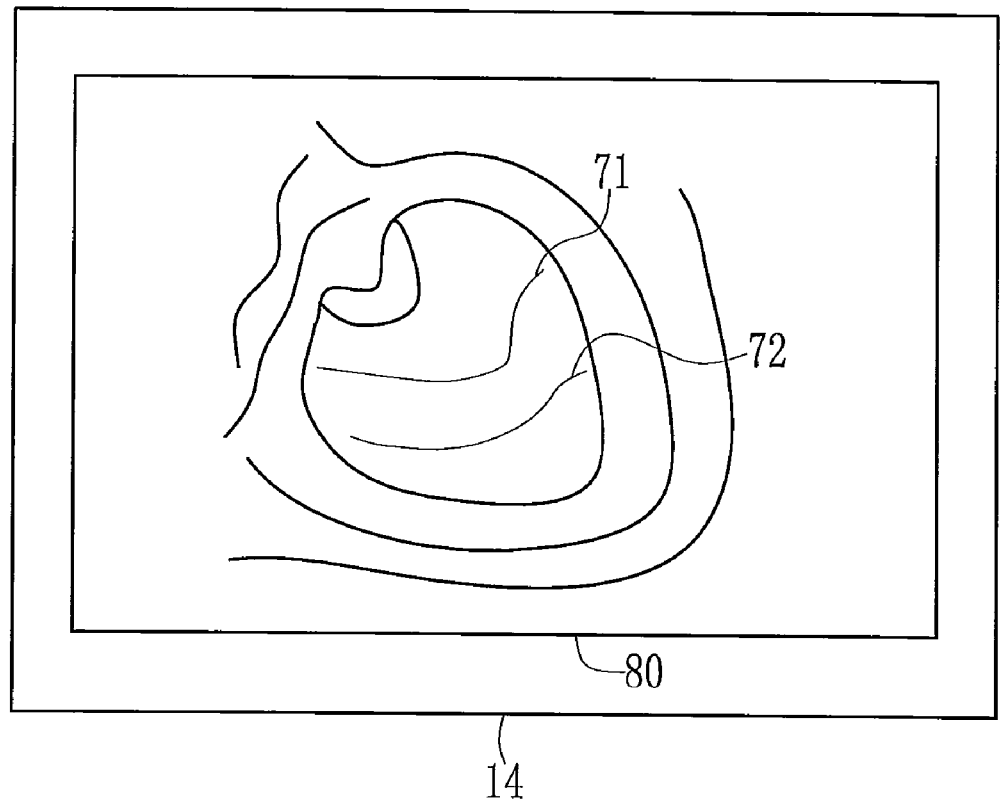
FIG. 7 shows the monitor displaying a broadband image in which contrast of a surface blood vessel region is reduced.

Compared to the broadband image 70 shown in FIG. 6, the visibility of the surface blood vessel region 71 is reduced in the broadband image 80 shown in FIG. 7. In the broadband image 80, the contrast of the surface blood vessel region 71 is reduced substantially equal to that of the deep blood vessel region 72. Accordingly, the surface blood vessel region 71 becomes inconspicuous in the broadband image 80, which allows the observation of a region other than the surface blood vessel region 71, for example, mucosal condition and the shape of mucosal surface.

To reduce the contrast, for example, low-pass filtering is performed. In the low-pass filtering, a high frequency component having a high spatial frequency of the surface blood vessel region 71 is cut or filtered out. Alternatively or in addition, other methods of reduction processing for controlling the visibility may be used. For example, the brightness value of the high brightness portion of the surface blood vessel region 71 may be reduced. In the contrast processing, the visibility of the surface blood vessel region 71 is reduced relative to the broadband image 70 with no contrast processing. In the contrast processing, it is not necessary to make the visibility of the surface blood vessel region 71 equal to that of the deep blood vessel region 72. The visibility of the surface blood vessel region 71 may be higher or lower than that of the deep blood vessel region 72.

The above-described processes are performed by the image processor 57 in the special mode. In the normal mode, on the other hand, the image processor 57 generates the broadband image 70 based on the broadband image data without extracting the blood vessel region and the contrast processing.

Figure 8:
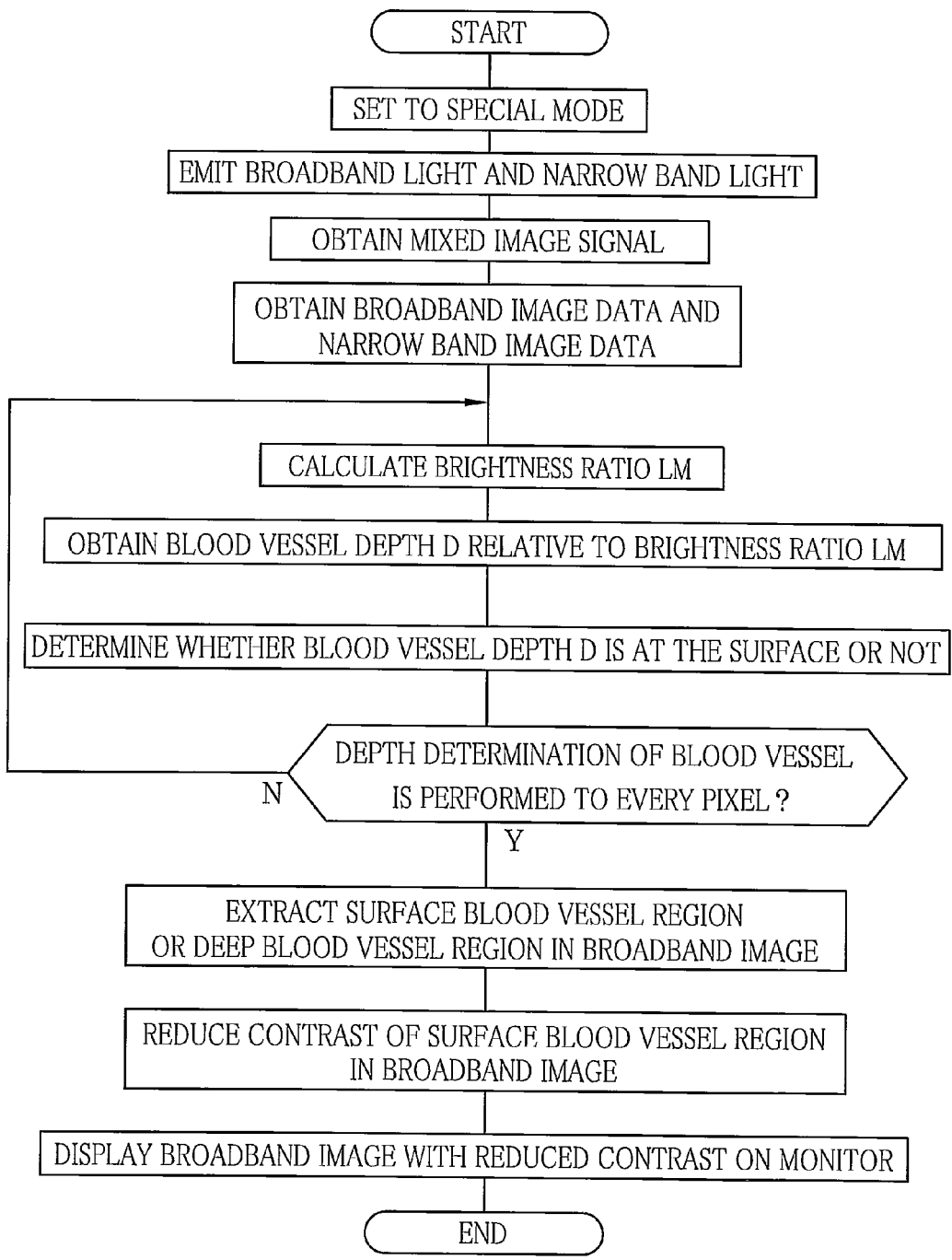
FIG. 8 is a flowchart showing steps in the present invention.

Next, referring to the flowchart of FIG. 8, an operation of the above configuration is described. In the normal mode, the shutter 31 is set in the retract position and only the broadband light source 30 is turned on, so the image capture is performed while the body cavity is illuminated only with the broadband light BB. The image processor 57 performs the image processing such as the color separation, the color interpolation, and the color correction to the broadband image signal obtained by the image capture to generate the broadband image data. The monitor 14 displays the broadband image 70 including the surface blood vessel region 71 with no contrast processing.

On the other hand, when the normal mode is switched to the special mode with the operation of a console or front panel 23, the controller 59 turns on the narrow band light source 33 in addition to the broadband light source 30. Thereby, both the broadband light BB and the narrow band light NB are emitted to the body cavity. An image is captured with the illumination of both the broadband light BB and the narrow band light NB. The mixed image signal of the captured image is obtained and sent to the DSP 55 via the AFE 45. The mixed image signal is composed of the R image signal only having the brightness value Broad_R, the G image signal only having the brightness value Broad_G, and the B image signal which is the sum of the brightness value Broad_B and the brightness value L1.

With the use of the brightness correlation information in the brightness correlation information storage 55a, the DSP 55 obtains the brightness value Broad_B which is in correlation with the brightness value Broad_G or Broad_R. Thereby, the broadband image signal composed of the brightness values Broad_B, Broad_G, and Broad_R is obtained. The broadband image signal is subjected to the various signal processes such as the color separation, the color interpolation, and the white balance adjustment to obtain the broadband image data. One frame of the broadband image data is stored in the frame memory 56.

The DSP 55 separates the brightness value Broad_B from the B image signal to obtain the narrow band image signal only having the brightness value L1. The narrow band image signal is subjected to the above-described signal processes to obtain the narrow band image data. One frame of the narrow band image data is stored in the frame memory 56.

After the broadband image data and the narrow band image data are stored in the frame memory 56, the brightness ratio calculator 61 identifies the picture elements in the same positions in the broadband image data and the narrow band image data, respectively. Then, the brightness ratio LM between the picture element in the narrowband image data and the corresponding picture element in the broadband image data is calculated. Next, based on the depth correlation information in the depth correlation information storage 62, the depth determining section 63 determines whether a blood vessel is included in each picture element and the depth of the blood vessel in each picture element. In the case where the brightness ratio LM calculated by the brightness ratio calculator 61 corresponds to a point P on the line segment La in the brightness ratio-blood vessel depth coordinate system, the blood vessel depth D is determined from the point P. The depth determining section 63 determines the blood vessel depth D is at the surface when the blood vessel depth D is smaller than a threshold value X, and the blood vessel depth D is at the subsurface depths when the blood vessel depth D is larger than the threshold value X.

The brightness ratio LM between the broadband image data and the narrow band image data is obtained with respect to every picture element in the broadband image data and the narrow band image data as described above. Then, for each brightness ratio LM, whether the blood vessel depth D corresponding to the brightness ratio LM is at the surface or not is determined. When the blood vessel depths D of all the picture elements are determined, the blood vessel region extractor 64 reads the broadband image data from the frame memory 56. From the broadband image corresponding to the read broadband image data, the blood vessel region extractor 64 extracts the surface blood vessel region and the deep blood vessel region. The surface blood vessel region contains the picture element including the blood vessel determined to be located at or close to the surface. The deep blood vessel region contains the picture element including the blood vessel determined to be located at the depths (subsurface). In the broadband image 70 in FIG. 6, the surface blood vessel region 71 and the deep blood vessel region 72 are extracted. In this embodiment, the deep blood vessel region is not subjected to specific image processing, so only the surface blood vessel region 71 may be extracted.

The image generator 65 performs contrast processing to the broadband image data to reduce the contrast of the surface blood vessel region 71. Thereby, the broadband image including the surface blood vessel region 71 with the reduced visibility is generated. As shown in FIG. 7, the broadband image 80 which has been subjected to the contrast processing is displayed on the monitor 14. Thus, it becomes possible to observe a normal visible image with the visibility of the surface blood vessels reduced.

The contrast of the surface blood vessel region 71 is reduced in the broadband image 80, so the surface blood vessel region 71 is made inconspicuous and does not interfere with the observation of a region of interest other than the surface blood vessel region 71. The depth of the blood vessel region is determined based on the brightness ratio between the narrow band image signal and the broadband image signal. Accordingly, the contrast of only the surface blood vessel region 71, which is likely to necessitate the contrast processing, is reduced. As a result, the information of the deep blood vessel region 72, which is naturally inconspicuous without the contrast processing, is maintained.

Because the blood vessel region is extracted using the narrow band image signal mainly containing the information on the surface of the tissue site, the surface blood vessel region is extracted with higher accuracy compared to a method for extracting the blood vessel region using only the broadband image signal. The contrast processing performed to the surface blood vessel region 71 in the broadband image 80 allows the operator or doctor to observe the overall condition of the tissue site including the surface blood vessel region 71 and the remaining region. Thus, the surface blood vessel region 71 and the remaining region are easily contrasted with each other and observed at a glance.

Figure 9:
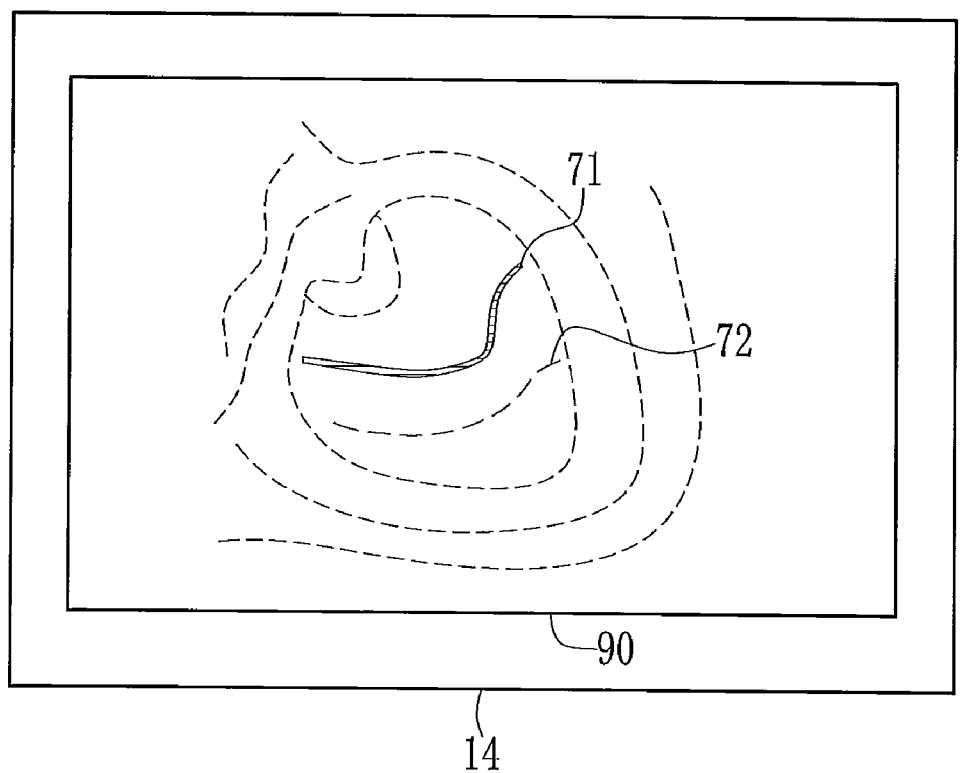
FIG. 9 shows a monitor displaying a broadband image in which contrast of a region other than the surface blood vessel region is reduced.

In the above embodiments described as examples, the visibility of the surface blood vessel region 71 is reduced. On the contrary, the visibility of the region other than the surface blood vessel region 71 may be reduced as shown in a broadband image 90 in FIG. 9. In FIG. 9, as a result of the contrast processing, the blood vessel depicted with the dotted lines has reduced visibility compared to that in the broadband image 70 shown in FIG. 6. Reducing the contrast of the region other than the surface blood vessel region 71 relatively increases the visibility of the surface blood vessel region 71. Thus, the surface blood vessel region 71 is enhanced. Such contrast processing is effective when the region of interest is the surface blood vessel region 71.

The conventional art only uses the narrow band light to obtain the narrow band image with the blood vessel region of a specific depth enhanced. Such art can be used to simply obtain the image with the enhanced surface blood vessel region, for example. In the present invention, unlike the conventional art, the image processing is performed to the broadband image having the amount of information larger than that of the narrow band image to enhance the blood vessel region. As a result, the observation of the region other than the blood vessel region becomes possible in addition to the observation of the blood vessel region. Displaying just one image having the enhanced blood vessel is more easily observable than displaying the broadband image and the narrow band image side by side.

Alternatively or in addition, the broadband image 90 in which the surface blood vessel is enhanced (see FIG. 9) and the broadband image 80 in which the surface blood vessel is made inconspicuous (see FIG. 7) may be displayed on the monitor 14 selectively or together. Operating the front panel 23 switches the display on the monitor 14.

In the above embodiments described as examples, the brightness ratio between the narrow band light in the wavelength range of 440±10 nm and the G component of the broadband light BB is used to extract the surface blood vessel region and the deep blood vessel region. Alternatively, for example, the narrow band light with wavelengths longer than the above embodiments and a color component of the broadband light BB may be used to distinguish and extract the medium-depth or intermediate-depth blood vessel region and the deep blood vessel region. In addition, the narrow band light in different wavelength ranges may be used in combination to extract the surface blood vessel region, the medium-depth blood vessel region, and the deep blood vessel region.

In the above embodiments, in the normal mode in which the contrast processing is not performed, the narrow band light source is turned off. In the special mode in which the contrast processing is performed, the narrow band light source is turned on. Alternatively, regardless of the modes, the broadband light source and the narrow band light source may be constantly turned on together. The mode may be switched between the normal mode and the special mode based on whether the image processor 57 performs the contrast processing.

In the above embodiments, the broadband light source is used to emit the broadband light BB. Instead of providing the broadband light source, a fluorescent member or phosphor device may be provided at an exit end of the light guide. The narrow band light NB excites the fluorescent member to generate the broadband light BB. The fluorescent member converts a part of the narrow band light NB into the broadband light BB, but passes through the remaining narrow band light NB. Thus, the broadband light BB and the narrow band light NB are emitted together without the use of the broadband light source. In using the fluorescent member to generate the broadband light BB, the wavelength range of the narrow band light NB is not limited to 440±10 nm as shown in the above embodiments. The narrow band light may be in a wavelength range capable of exciting the white broadband light BB, and in a wavelength range which is not sensed by the G pixel and the R pixel (for example, 400±10 nm). A light emission apparatus combining the fluorescent member and the light source such as the GaN semiconductor is commercially available under the product name MicroWhite, for example. The narrow band light NB from the light source excites the fluorescent member to emit the white broadband light BB.

In the above embodiments, the depth of the blood vessel region (blood vessel depth) is determined based on the brightness ratio between the broadband image data and the narrow band image data. Alternatively, the blood vessel depth may be obtained using the narrow image data in which the blood vessel region of a specific depth is enhanced as in the conventional art. For example, in the blue narrow band image data, the surface blood vessel region is enhanced. When the blood vessel region is extracted using the difference between the brightness value of the blood vessel region and the brightness value of the remaining region in the narrow band image data, there is a high possibility that the identified blood vessel region is located at the surface of the tissue site. Based on the extracted surface blood vessel region, the contrast processing is performed to the broadband image.

The above described method based on the conventional art is inferior in accuracy of determining the blood vessel depth compared to the above embodiments of the present invention, because the narrow band image data also includes medium-depth and deep blood vessel regions other than the surface blood vessel region. Although the medium-depth and deep blood vessel regions have low visibility, there is a high possibility that the medium-depth and deep blood vessel regions are mistaken for the surface blood vessel regions. Accordingly, the above-described methods for determining the blood vessel depth based on the brightness ratio are superior to the conventional method.

In this embodiment, the blood vessel region is extracted using both the broadband image data and the narrow band image data. Alternatively, the blood vessel region may be extracted only using the narrow band image data. This method has the following advantage. Because the broadband light BB includes light with long wavelengths which penetrates deeper into the tissue site, the broadband image data has an amount of information larger than that of the narrow band image data. Accordingly, when the blood vessel region is extracted only using the broadband image data, there is a high possibility that the region other than the blood vessel region may be mistaken for the blood vessel region.

On the other hand, because the narrow band light NB is a single color light with short wavelengths with a small penetration depth, the narrow band image data has little information of the tissue site at the subsurface depths. Based on the narrow band image data, the surface blood vessel region can be extracted with high accuracy. Accordingly, to prevent the misrecognition of the blood vessel region, the blood vessel region extracted using the narrow band image data is given higher priority to that based only on the broadband image data. To extract the blood vessel region, a difference between the brightness value of the blood vessel and the brightness value of a portion other than the blood vessel may be used. Alternatively or in addition, a pattern recognition may be used.

In the above embodiments described as examples, two modes, the normal mode and the special mode, are provided. In the normal mode, the broadband image is displayed without the contrast processing. In the special mode, the broadband image which has been subjected to the contrast processing is displayed. One or more modes may be provided in addition to the above modes, for example, a mode in which a narrow band image is generated and displayed based on the narrow band image data.

In the above embodiments, the image capture is performed while the broadband light and the narrow band light are emitted simultaneously. One frame of the mixed image signal obtained by the image capture is separated into the broadband image signals and the narrow band image signal. Alternatively, the broadband light and the narrow band light may be selectively emitted. In this case, the broadband image signal and the narrow band image signal are obtained separately. The broadband image signal is obtained with the illumination of the broadband light, and the narrow band image signal is obtained with the illumination of the narrow band light.

In the above embodiments, the mixed image signal is separated into the broadband image data and the narrow band image data to obtain the brightness ratio therebetween. The blood vessel depth is determined using the brightness ratio. Alternatively or in addition, the blood vessel depth can be determined using a brightness ratio between the signal outputted from the B pixel of the mixed image signal and the signal outputted from the G pixel of the mixed image signal. In the above embodiments, the mixed image signal is separated into the narrow band light component and the broadband light component to obtain the broadband image signal. Alternatively, the mixed image signal may be subjected to a predetermined conversion to obtain the broadband image signal. In this case, the narrow band image signal is obtained using the mixed image signal and the broadband image signal.

The present invention can be applicable to the electronic endoscope having the insert section, and also to a capsule-type electronic endoscope having an image sensor such as a CCD incorporated in a capsule, and an electronic endoscope for imaging of a body cavity other than the digestive tract, for example, respiratory tract.

Various changes and modifications are possible in the present invention and may be understood to be within the present invention.

What is claimed is:

1. An electronic endoscope system comprising:
   an emission section for emitting white broadband light and narrow band light simultaneously or sequentially to illuminate a tissue site in a body cavity, the tissue site including a blood vessel, the broadband light having a wavelength range from blue to red, the narrow band light being in a specific wavelength range;
   an imaging section for capturing an image of the tissue site during the illumination and outputting image signals in time order, the imaging section having a blue pixel, a green pixel, and a red pixel arranged therein, the blue pixel sensing blue light to generate a blue color signal, the green pixel sensing green light to generate a green color signal, the red pixel sensing red light to generate a red color signal;
   a data obtaining section for obtaining broadband image data and narrow band image data or mixed image data based on the image signals, the broadband image data corresponding to the image capture under the broadband light, the narrow band image data corresponding to the image capture under the narrow band light, and the mixed image data being a combination of the broadband image data and the narrow band image data;
   a brightness ratio calculator for calculating a brightness ratio between the broadband image data and the narrow band image data or a brightness ratio between the blue color signal and the green color signal in the mixed image data on a picture element basis;
   a depth correlation information storage for storing depth correlation information between the brightness ratio and a depth of the blood vessel;
   a depth determining section for referring to the depth correlation information to determine whether the picture element includes the blood vessel and the depth of the blood vessel on the picture element basis with the use of the calculated brightness ratio;
   a blood vessel region extractor for extracting a specific blood vessel region based on the determined depth of the blood vessel; and
   an image processing section for performing image processing to the specific blood vessel region or a region other than the specific blood vessel region within a broadband image based on the broadband image data.

2. The electronic endoscope system of claim 1, further including an electronic endoscope, a processing apparatus connected to the electronic endoscope, and a light source apparatus connected to the electronic endoscope;
   and wherein the electronic endoscope is provided with the emission section and the imaging section;
   and wherein the processing apparatus is provided with the data obtaining section, the brightness ratio calculator, the depth correlation information storage, the depth determining section, the blood vessel region extractor, and the image processing section;
   and wherein the light source apparatus is provided with a light source for generating the broadband light and the narrow band light, and the broadband light and the narrow band light are guided to the emission section through a light guide in the electronic endoscope and emitted from the emission section to the tissue site.

3. The electronic endoscope system of claim 1, wherein the specific blood vessel region is a surface blood vessel located at the small depth.

4. The electronic endoscope system of claim 3, wherein the image processing is reduction of visibility.

5. The electronic endoscope system of claim 4, wherein the reduction of the visibility is to reduce contrast.

6. The electronic endoscope system of claim 4, wherein the broadband light is in a wavelength range from approximately 470 nm to 700 nm, and the narrow band light is in a wavelength range of 440±10 nm or 400±10 nm.

7. The electronic endoscope system of claim 4, further comprising a display section for displaying the broadband image processed in the image processing section.

8. A processing apparatus connected to an electronic endoscope, the electronic endoscope having an imaging section for outputting image signals in time order, the imaging section having a blue pixel, a green pixel, and a red pixel arranged therein, the blue pixel sensing blue light to generate a blue color signal, the green pixel sensing green light to generate a green color signal, the red pixel sensing red light to generate a red color signal, the imaging section capturing an image of a tissue site in a body cavity while white broadband light and narrow band light are emitted to the tissue site simultaneously or sequentially, the tissue site including a blood vessel, the white broadband light having a wavelength range from blue to red, the narrow band light being in a specific wavelength range, the processing apparatus comprising:
- a data obtaining section for obtaining broadband image data and narrow band image data or mixed image data based on the image signals, the broadband image data corresponding to the image capture under the broadband light, the narrow band image data corresponding to the image capture under the narrow band light, and the mixed image data being a combination of the broadband image data and the narrow band image data;
- a brightness ratio calculator for calculating a brightness ratio between the broadband image data and the narrow band image data or a brightness ratio between the blue color signal and the green color signal in the mixed image data on a picture element basis;
- a depth correlation information storage for storing depth correlation information between the brightness ratio and a depth of the blood vessel;
- a depth determining section for referring to the depth correlation information to determine whether the picture element includes a blood vessel and the depth of the blood vessel on the picture element basis with the use of the calculated brightness ratio;
- a blood vessel region extractor for extracting a specific blood vessel region based on the determined depth of the blood vessel; and
- an image processing section for performing image processing to the specific blood vessel region or a region other than the specific blood vessel region within a broadband image based on the broadband image data.

9. An image processing method of an endoscopic image, comprising the steps of:
- capturing an image of a tissue site in a body cavity while white broadband light and narrow band light are emitted simultaneously or sequentially to the tissue site to obtain image signals in time order, the tissue site including a blood vessel, the broadband light having a wavelength range from blue to red, the narrow band light being in a specific wavelength range, the image signals including a blue color signal, a green color signal, and a red color signal;
- obtaining broadband image data and narrow band image data or mixed image data based on the image signals, the broadband image data corresponding to the image capture under the broadband light, the narrow band image data corresponding to the image capture under the narrow band light, and the mixed image data being a combination of the broadband image data and the narrow band image data;
- calculating a brightness ratio between the broadband image data and the narrow band image data or a brightness ratio between the blue color signal and the green color signal in the mixed image data on a picture element basis;
- referring to a depth correlation information between the brightness ratio and a depth of the blood vessel and determining whether the picture element includes a blood vessel and the depth of the blood vessel on the picture element basis with the use of the calculated brightness ratio;
- extracting a specific blood vessel region based on the determined depth of the blood vessel; and
- performing image processing to the specific blood vessel region or a region other than the specific blood vessel region within a broadband image based on the broadband image data.

* * * * *